(12) United States Patent
Rand (10) Patent No.: US 7,461,650 B1
(45) Date of Patent: Dec. 9, 2008

(54) MEDICAMENT DISPENSER

(75) Inventor: Paul Kenneth Rand, Ware (GB)

(73) Assignee: Glaxo Group Limited, Greenford, Middlesex (GB)

( * ) Notice: Subject to any disclaimer, the term of this patent is extended or adjusted under 35 U.S.C. 154(b) by 155 days.

(21) Appl. No.: 10/110,958

(22) PCT Filed: Sep. 28, 2000

(86) PCT No.: PCT/EP00/09640

§ 371 (c)(1),
(2), (4) Date: Apr. 18, 2002

(87) PCT Pub. No.: WO01/28615

PCT Pub. Date: Apr. 26, 2001

(30) Foreign Application Priority Data

Oct. 21, 1999 (GB) .................................. 9924780.1

(51) Int. Cl.
| | |
|---|---|
| A61M 11/00 | (2006.01) |
| A61M 15/00 | (2006.01) |
| A61M 16/10 | (2006.01) |
| B05B 1/08 | (2006.01) |
| B05B 3/04 | (2006.01) |
| B05B 17/06 | (2006.01) |
| B65D 83/06 | (2006.01) |
| B65D 83/14 | (2006.01) |
| B01F 11/02 | (2006.01) |

(52) U.S. Cl. .......................... 128/200.23; 128/200.14; 128/200.16; 128/203.12; 239/102.2; 222/161; 222/196; 222/221; 222/402.1; 366/108

(58) Field of Classification Search ............ 128/200.14, 128/200.16, 200.23, 203.12, 200.11, 200.17, 128/203.15, 203.19, 203.21; 239/102.2; 222/402.1, 160, 161, 167, 196, 216, 221; 366/108, 110–116, 241, 605, 127, 117–118, 366/212, 240, 197–218, 237, 239

See application file for complete search history.

(56) References Cited

U.S. PATENT DOCUMENTS

| | | | |
|---|---|---|---|
| 2,877,994 A | | 3/1959 | Jones et al. |
| 3,042,310 A | | 7/1962 | Reinhold et al. |
| 3,384,354 A | | 5/1968 | Migule et al. |
| 3,456,644 A | * | 7/1969 | Thiel ..................... 128/200.23 |

(Continued)

FOREIGN PATENT DOCUMENTS

CA          879586       *    8/1971

(Continued)

OTHER PUBLICATIONS

Patent Abstract of Japan, vol. 011, No. 054 (M-563), Feb. 19, 1987 & JP 61217431 A (Kobe Steel Ltd.), Sep. 27, 1986 Abstract.

*Primary Examiner*—Justine R. Yu
*Assistant Examiner*—Annette F. Dixon
(74) *Attorney, Agent, or Firm*—Robert J. Smith (57) ABSTRACT

A medicament dispenser including a housing, a medicament container having a dispensing outlet; an agitator for agitating the contents; and a driver for driving the agitator independent of any container movement. The driver includes an energy storeage for storing energy releasable to drive the agitator. The medicament container may be a metered dose inhaler or delivering a suitable inhalable medicament.

26 Claims, 4 Drawing Sheets

U.S. PATENT DOCUMENTS

| | | | | |
|---|---|---|---|---|
| 3,565,070 | A | * | 2/1971 | Hanson et al. ......... 128/200.23 |
| 3,598,294 | A | * | 8/1971 | Hedrick et al. ........... 222/402.2 |
| 3,636,949 | A | * | 1/1972 | Kropp ................... 128/200.23 |
| 3,789,843 | A | * | 2/1974 | Armstrong et al. ..... 128/200.23 |
| 3,863,903 | A | | 2/1975 | Brehmer et al. |
| 3,971,377 | A | | 7/1976 | Damani |
| 4,061,315 | A | | 12/1977 | Eitzen et al. |
| 4,184,778 | A | | 1/1980 | Terrels |
| 4,240,418 | A | * | 12/1980 | Rosskamp et al. ..... 128/203.15 |
| 4,259,021 | A | | 3/1981 | Goudy, Jr. |
| 4,300,554 | A | | 11/1981 | Hessberg et al. |
| 4,502,342 | A | | 3/1985 | Kraft et al. |
| 4,518,103 | A | | 5/1985 | Lim et al. |
| 4,612,291 | A | | 9/1986 | Dawes |
| 4,648,393 | A | * | 3/1987 | Landis et al. .......... 128/200.23 |
| 4,759,635 | A | | 7/1988 | MacMichael et al. |
| 4,808,006 | A | | 2/1989 | Kaufeler |
| 4,858,759 | A | | 8/1989 | Mauthe et al. |
| 4,868,801 | A | | 9/1989 | Dold |
| 4,888,607 | A | * | 12/1989 | Stutz et al. .................. 396/625 |
| 5,027,808 | A | * | 7/1991 | Rich et al. ............. 128/203.23 |
| 5,071,040 | A | | 12/1991 | Laptewicz, Jr. |
| 5,159,224 | A | * | 10/1992 | Kramer et al. ......... 310/323.09 |
| 5,221,025 | A | * | 6/1993 | Privas ........................... 222/1 |
| 5,347,998 | A | * | 9/1994 | Hodson et al. ......... 128/200.23 |
| 5,352,036 | A | | 10/1994 | Haber et al. |
| 5,397,178 | A | | 3/1995 | Konietzko |
| 5,449,493 | A | | 9/1995 | Rokugawa et al. |
| 5,451,105 | A | | 9/1995 | Koering |
| 5,487,378 | A | | 1/1996 | Robertson et al. |
| 5,608,693 | A | | 3/1997 | Richards |
| 5,622,166 | A | | 4/1997 | Eisele et al. |
| RE35,552 | E | * | 7/1997 | Lankinen ............... 128/203.12 |
| 5,727,541 | A | | 3/1998 | Rowland |
| 5,743,250 | A | | 4/1998 | Gonda et al. |
| 5,806,526 | A | * | 9/1998 | Rhoad ........................ 128/864 |
| 5,842,786 | A | | 12/1998 | Solomon |
| 5,879,081 | A | | 3/1999 | Chordia |
| 5,894,841 | A | | 4/1999 | Voges |
| 6,116,234 | A | * | 9/2000 | Genova et al. ......... 128/200.23 |
| 6,119,688 | A | * | 9/2000 | Whaley et al. ......... 128/203.15 |
| 6,293,693 | B1 | | 9/2001 | Rodgers et al. |
| 6,308,704 | B1 | * | 10/2001 | Wennerberg ........... 128/203.15 |
| 6,378,518 | B1 | | 4/2002 | Miekka et al. |
| 6,387,077 | B1 | * | 5/2002 | Klibanov et al. ............. 604/181 |
| 6,394,086 | B1 | | 5/2002 | Barnes et al. |
| 6,454,193 | B1 | | 9/2002 | Busick et al. |
| 6,474,563 | B2 | | 11/2002 | Pletcher et al. |
| 6,729,559 | B2 | | 5/2004 | Zanma et al. |
| 7,185,648 | B1 | | 3/2007 | Rand |
| 2003/0056789 | A1 | | 3/2003 | Takano et al. |

FOREIGN PATENT DOCUMENTS

| | | | |
|---|---|---|---|
| DE | 3115568 | | 4/1982 |
| EP | 00966101.8 | | 12/2005 |
| GB | 997 088 A | | 6/1965 |
| GB | 997088 A | | 6/1965 |
| GB | 2129322 | | 5/1984 |
| GB | 2262452 A | * | 6/1993 |
| WO | WO95/30607 | | 11/1995 |
| WO | WO 96/08284 | | 3/1996 |
| WO | WO97/44080 | * | 11/1997 |
| WO | 99 47195 A | | 9/1999 |
| WO | 9947195 A | | 9/1999 |
| WO | WO 00/44423 | | 8/2000 |

* cited by examiner

MEDICAMENT DISPENSER

The instant application is filed under 35 U.S.C. § 371 as the United States National Phase Application of International Application No. PCT/EP00/09640 filed 28 Sep. 2000 claiming priority from GB 9924780.1 filed 21 Oct. 1999.

TECHNICAL FIELD

This invention relates to a medicament dispenser comprising a housing and a medicament container. The dispenser includes an agitator for agitating the medicament container by release of stored energy. The dispenser is particularly suitable for use as an inhalation device.

BACKGROUND TO THE INVENTION

Known medicament dispensers comprise a medicament container having a dispensing outlet for dispensing of the medicament therefrom. Such medicament dispensers often require the patient to agitate the contents thereof prior to dispensing to ensure ready and uniform dispensing of the medicament. The agitation involves a manual shaking action.

Agitation is particularly required where the dispenser comprises medicament as a suspension in a propellant formulation. A well-known example of this type is the metered dose inhaler for dispensing of respiratory medicament which comprises an aerosol container having a dispensing valve. The medicament is comprised within the aerosol container in the form of a suspension comprising propellant and optionally other additives such as solvents or surfactants. Such suspensions have a tendency to settle out, sediment or cream. A pre-dispensing agitation step is necessary to re-establish a uniform suspension so that uniform dispensing of medicament may be achieved.

Agitation can also be required where the medicament is in powder form. It is well known that powders can tend to settle out, agglomerate or even cake on storage. The agitation therefore performs the function of breaking up any agglomerates or cakes that may have formed, and thereby ensures that the powder is readily dispensable.

Various suggestions have been made to enhance the manual shaking action to maximise the effect of agitation.

PCT Patent Application No. WO95/30607 describes a metered dose dispensing valve including a movable agitator in the metering chamber. Manual shaking of the valve causes movement of the agitator therein which is stated to assist mixing of the drug suspension in the metering chamber.

PCT Patent Application No. WO96/08284 describes an inhalation device for dispensing powder form medicament including a movable weight which is configured to strike an anvil upon manual shaking of the device. The striking action causes a jolt which acts such as to assist transfer of the powder from a reservoir container to a metering recess formed in a dosing member.

Whilst manual shaking is a generally effective means for providing agitation it is sometimes inconvenient for the patient. In social situations, the patient often wishes to administer their medicament discretely and without drawing attention to themselves. Manual shaking of the dispenser is difficult to perform in a discrete fashion. This can lead to patient embarrassment. There is also always the possibility that the patient forgets to shake the dispenser, or does so inadequately, thereby affecting the medicament dose deliverable.

The Applicants have now developed a medicament dispenser which requires little or no manual shaking. The dispenser comprises a medicament container within a housing. The dispenser includes an agitator for agitating the medicament container and a driver for driving the agitator. The driver comprises an energy store for storing energy which energy is releasable to drive the agitator. The dispenser therefore provides for agitation of the medicament container and contents thereof without requiring shaking by the patient.

SUMMARY OF INVENTION

According to one aspect of the present invention there is provided a medicament dispenser comprising a housing; a medicament container having a dispensing outlet; an agitator for agitating said container; and a driver for driving said agitator, wherein said driver comprises an energy store for storing energy which energy is releasable to drive the agitator.

Preferably, the container is mounted for movement within the housing.

In one aspect, the container is rotatable within the housing.

In another aspect, the container is movable in a reciprocating fashion within the housing.

Preferably, the agitator couples mechanically to the container.

In one aspect, the agitator couples to the container through a cam arrangement. The cam arrangement may comprise a stepped cam or a snail cam.

In another aspect, the agitator couples to the container through a con-rod and crank arrangement.

In a further aspect, the agitator couples to the container through a gear drive arrangement.

In a further aspect, the agitator couples magnetically to the container. Preferably, either or both of the agitator or the container comprises magnetic material or material which is magnetically inductive, that is to say material into which magnetism can be induced. The material may be permanently or non-permanently magnetisable.

In a further aspect, the agitator couples pneumatically to the container.

In a further aspect, the agitator couples hydraulically to the container.

In a further aspect, the agitator comprises a multi-component strip or wire which is deformable in response to electrical current flow.

Suitable multi-component strips typically comprise a plurality of layers of material, each material having a different coefficient of thermal expansion. Preferred examples of multi-component strips include strips comprising multiple layers of different metals (e.g. bimetallic strips) and strips comprising at least one piezoelectric or piezoresistive material. Suitable piezoelectric materials include piezoelectric ceramics, such as compounds of lead zirconate and lead titanate, and piezoelectric crystals which are generally polycrystalline ferroelectric materials with the perovskite structure.

Suitable multi-component wires typically comprise alloys of two or more metals wherein one or more of the metals undergoes a temperature induced phase change in response to electrical current flow. Preferred examples of multi-component wires include those comprised of alloys of titanium and nickel which contract when electric current is applied.

Preferably, the agitator provides wave energy to the container. More preferably, the agitator is an acoustic wave energy generator or a resonant wave energy generator.

Preferably, the container comprises a guide to guide fluid flow within the container. More preferably, the guide comprises a vane arrangement or a movable impeller.

Preferably, the dispenser comprises a stop mechanism for stopping movement of the container. More preferably, the stop mechanism is capable of providing a shock stop to the container.

Preferably, the energy store comprises a biasable resilient member. More preferably, the biasable resilient member is a spring.

Preferably, the energy store comprises a clockwork mechanism.

Preferably, the energy store comprises a battery.

Preferably, the driver is responsive to a patient-actuable trigger. More preferably, the trigger comprises a button, switch or lever arrangement. Most preferably, the trigger comprises a sensor which senses the breath of a patient.

In one aspect, the sensor comprises a breath-movable element which is movable in response to the breath of a patient. More preferably, the breath-movable element is selected from the group consisting of a vane, a sail, a piston and an impeller.

In another aspect, the sensor comprises a pressure sensor for sensing the pressure profile associated with the breath of a patient.

In a further aspect, the sensor comprises an airflow sensor for sensing the airflow profile associated with the breath of a patient.

In a further aspect, the sensor comprises a temperature sensor for sensing the temperature profile associated with the breath of a patient.

In a further aspect, the sensor comprises a moisture sensor for sensing the moisture profile associated with the breath of a patient.

In a further aspect, the sensor comprises a gas sensor for sensing the oxygen or carbon dioxide profile associated with the breath of a patient.

Preferably, dispensing from the dispensing outlet is responsive to a second patient-actuable trigger.

Preferably, the patient-actuable triggers are coupled such that agitation and dispensing occurs in a sequential fashion.

In one aspect, the container is an aerosol container. Preferably, the container comprises a metering valve at the dispensing outlet.

Preferably, the aerosol container comprises a suspension of a medicament in a propellant. More preferably, the propellant comprises liquefied HFA134a, HFA-227 or carbon dioxide. The medicament can be selected from the group consisting of albuterol, salmeterol, fluticasone propionate, beclomethasone dipropionate, salts or solvates thereof and any mixtures thereof.

In another aspect, the aerosol container comprises a compressed gas, preferably compressed air.

BRIEF DESCRIPTION OF THE INVENTION

The invention will now be described further with reference to the accompanying drawings in which.

DETAILED DESCRIPTION OF THE INVENTION

Figure 1A:
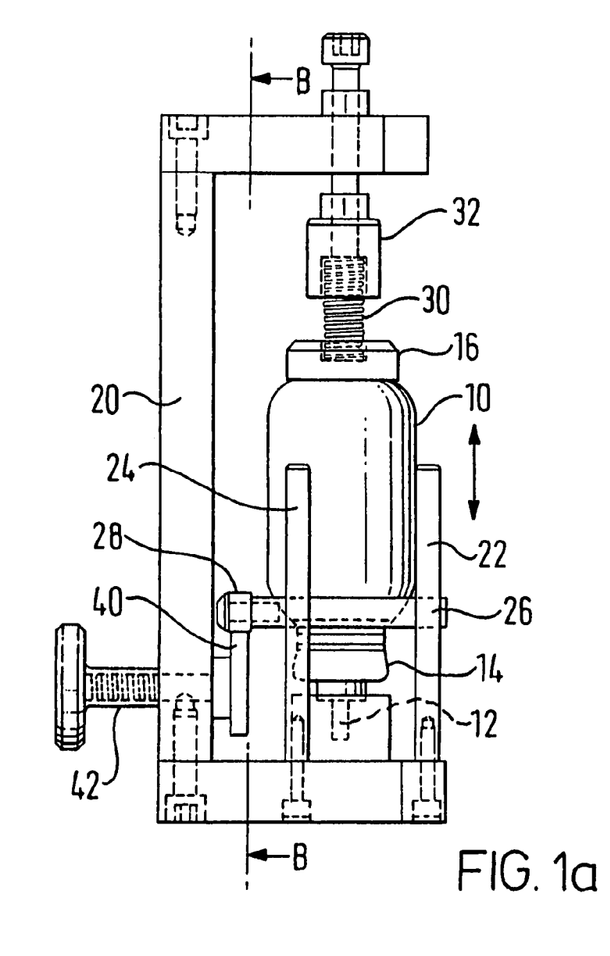
FIGS. 1a and 1b show sectional views of a first medicament dispenser in accord with the present invention.
Figure 1B:
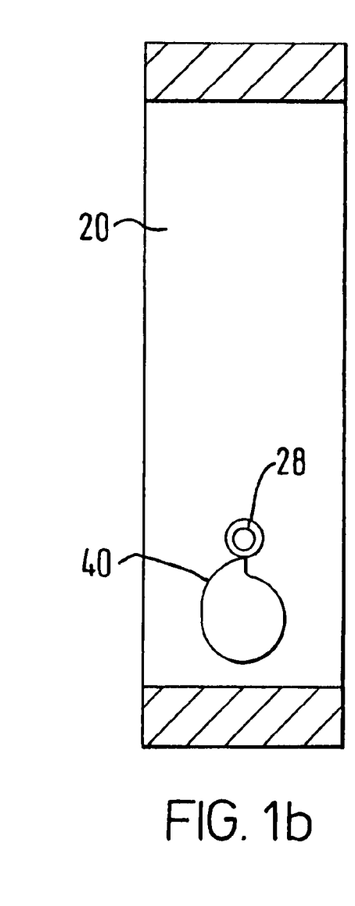

FIGS. 1a and 1b show a medicament dispenser mounted within an actuator housing 20. The actuator housing 20 is shown in the form of a laboratory test rig. It will be appreciated that the test rig can be adapted by way of workshop modifications to form a more recognizable product housing (e.g. an inhaler device product housing) incorporating the same functional elements. FIG. 1b shows a sectional view of the dispenser and housing 20 taken along section B—B of FIG. 1a.

The medicament dispenser is suitable for use in a metered dose inhaler (MDI) for delivery of inhalable medicament. The dispenser comprises an aerosol can 10 having a dispenser outlet in the form of a metering valve 12. The valve gasket 14 is fixedly attached (typically by crimping) to the aerosol can body 10. The can suitably comprises a suspension of medicament in a propellant.

The can 10 is mounted within a cradle comprising fixed uprights 22, 24 and base section 26 which has a central aperture for receipt of the neck of the can such that the can 10 sits therein. The base section 26 is freely movable up and down on the uprights 22, 24. The base of the can 10 is provided with an acetal pad 16 which receives compression spring 30. The compression spring 30 connects with pre-load adjuster 32 which is itself fixed to the housing 20. Overall, it may thus be appreciated that the can 10 is mounted within the housing 20 such that it is movable up and down but is under the influence of a generally downward spring bias.

The base section 26 of the can-receiving cradle is also provided with a cam follower 28 which follows snail cam 40. Snail cam 40 is itself axially mounted to the housing 20 and is drivable by the action of torsion spring drive 42. In other embodiments, the torsion spring drive 42 may be replaced by another suitable source of drive energy such as a clockwork or battery-driven electric motor.

Agitation of the aerosol can 10 is achievable by the following steps. The torsion spring drive 42 is actuated to drivably rotate the snail cam 40. The cam follower 28 follows the path defined by the snail cam 40 such that the base section 26 and can 10 sitting therein are initially moved gradually upwards but then suddenly released downwards. The can 10 is thus submitted to a shock downward movement which agitates the contents thereof.

Figure 2A:
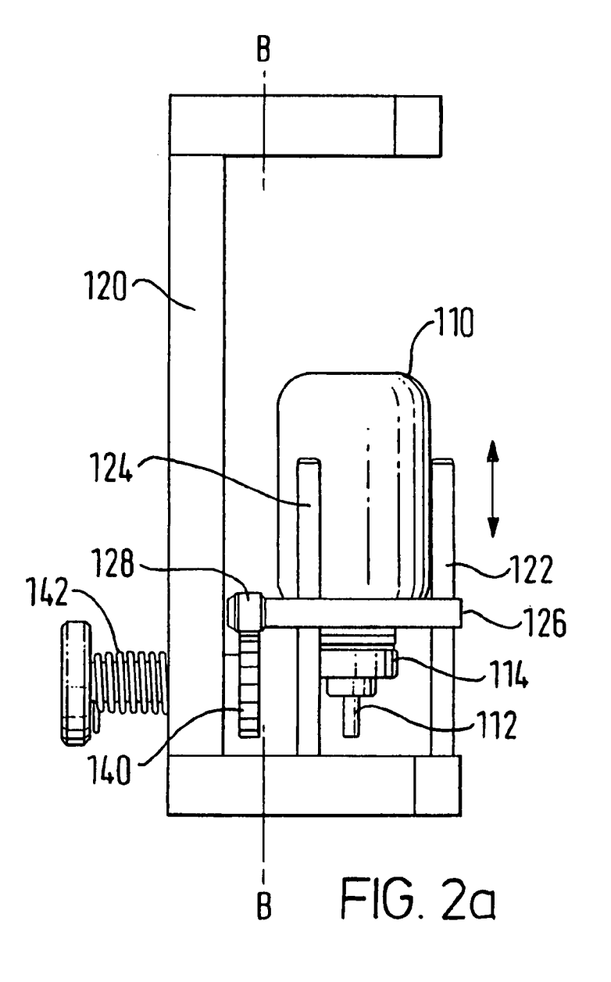
FIGS. 2a and 2b show sectional views of a second medicament dispenser in accord with the present invention.
Figure 2B:
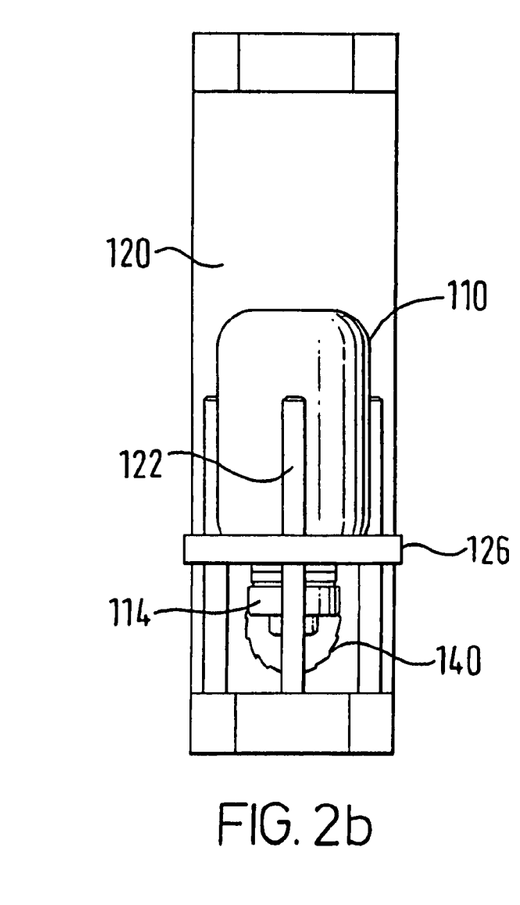

FIGS. 2a and 2b show a medicament dispenser herein mounted within an actuator housing 120. The actuator housing 120 is shown in the form of a laboratory test rig. It will be appreciated that the test rig can be adapted by way of workshop modifications to form a more recognisable product housing incorporating the same functional elements. FIG. 2b shows a sectional view of the dispenser and housing 120 taken along section B—B of FIG. 2a.

The medicament dispenser is suitable for use in a metered dose inhaler (MDI) for delivery of inhalable medicament. The dispenser comprises an aerosol can 110 having a dispenser outlet in the form of a metering valve 112. The valve gasket 114 is fixedly attached (typically by crimping) to the aerosol can body 110. The can suitably comprises a suspension of medicament in a propellant.

The can 110 is mounted within a cradle comprising fixed uprights 122, 124 and base section 126 which has a central aperture for receipt of the neck of the can such that the can 110 sits therein. The base section 126 is freely movable up and down on the uprights 122, 124. In other embodiments, the can 110 may be biased in a generally downward direction, for example by a compression spring arrangement as shown in FIGS. 1a and 1b.

The base section 126 of the can-receiving cradle is also provided with a cam follower 128 which follows stepped cam 140. A suitable stepped cam has 9 steps per 360 degree ° and 0.45 mm drop per step. The stepped cam 140 is itself axially mounted to the housing 120 and is drivable by the action of torsion spring drive 142. In other embodiments, the torsion spring drive 142 may be replaced by another suitable drive motor such as a clockwork or electric motor.

Agitation of the aerosol can 110 is achievable by the following steps. The torsion spring drive 142 is actuated to drivably rotate the stepped cam 140. The cam follower 128 follows the path defined by the stepped cam 140. The base section 126 and can 110 sitting therein thus follow stepped movements comprising a gradually upward movement and more sudden downwards release. The can 110 is thus submitted to regularly stepped downward shock movements which agitate the contents thereof.

Figure 3A:
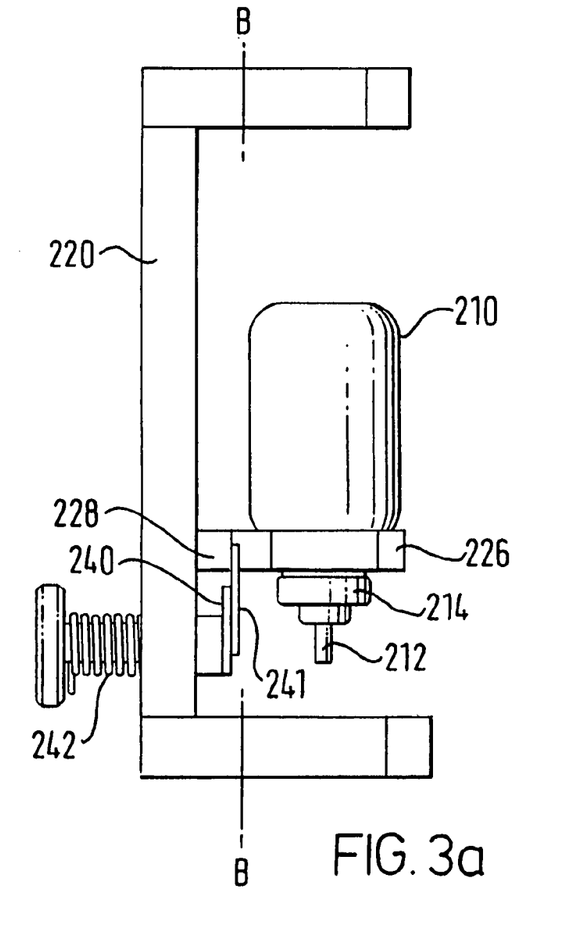
FIGS. 3a and 3b show sectional views of a third medicament dispenser in accord with the present invention.
Figure 3B:
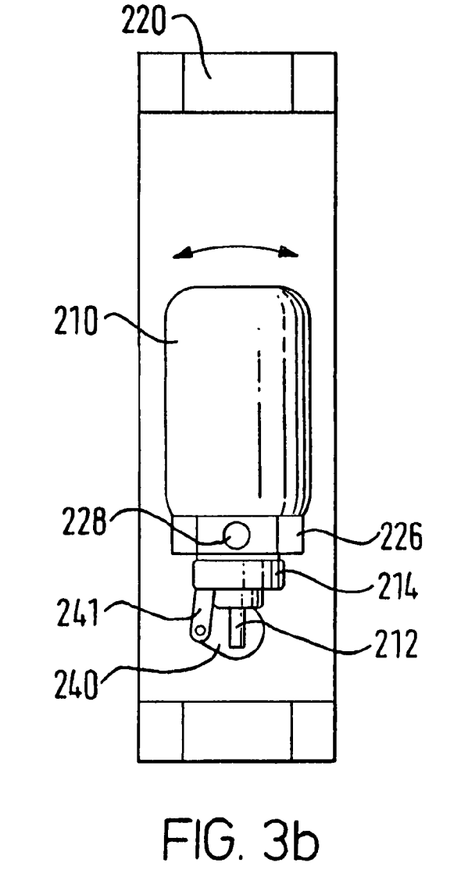

FIGS. 3*a* and 3*b* show a medicament dispenser herein mounted within an actuator housing 220. The actuator housing 220 is shown in the form of a laboratory test rig. It will be appreciated that the test rig can be adapted by way of workshop modifications to form a more recognizable product housing incorporating the same functional elements. FIG. 3*b* shows a sectional view of the dispenser and housing 220 taken along section B—B of FIG. 3*a*.

The medicament dispenser is suitable for use in a metered dose inhaler (MDI) for delivery of inhalable medicament. The dispenser comprises an aerosol can 210 having a dispenser outlet in the form of a metering valve 212. The valve gasket 214 is fixedly attached (typically by crimping) to the aerosol can body 210. The can suitably comprises a suspension of medicament in a propellant.

The can 210 is mounted within cradle 226 which has a central aperture for receipt of the neck of the can such that the can 210 sits therein. The cradle 226 is movably mounted to the housing 220 through axle 228. The axle 228 connects with con-rod 241 which in-turn connects with crank 240. The crank 240 is axially mounted to the housing 220 and is drivable by the action of torsion spring drive 242. Overall, it may be appreciated that cradle 226 and can 210 are movable in a reciprocating (i.e. rocking) movement on axle 228 responsive to movement of the con-rod 241 and crank 240 arrangement. Drive energy is provided by the torsion spring 242. In other embodiments, the torsion spring drive 242 may be replaced by another suitable drive motor such as a clockwork or electric motor.

Agitation of the aerosol can 210 is achievable by the following steps. The torsion spring drive 242 is actuated to drivably rotate the crank 240 and con-rod 241. The movement of con-rod 241 in turn results in a rocking movement of the cradle 226 and can 220 on axle 228. The rocking movement agitates the can 210 and contents thereof.

Figure 4A:
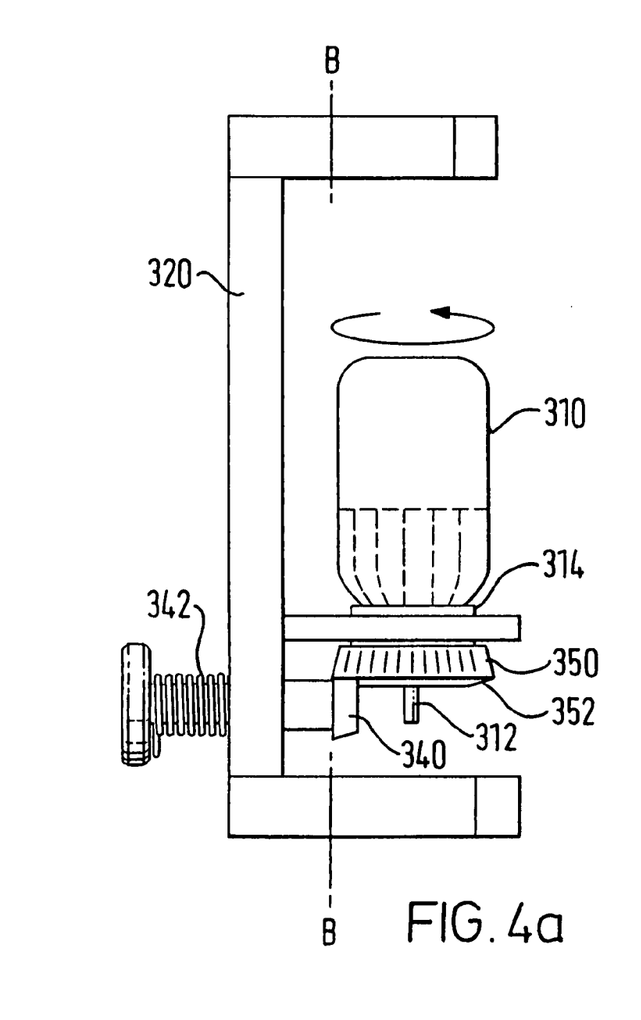
FIGS. 4a and 4b show sectional views of a fourth medicament dispenser in accord with the present invention.
Figure 4B:
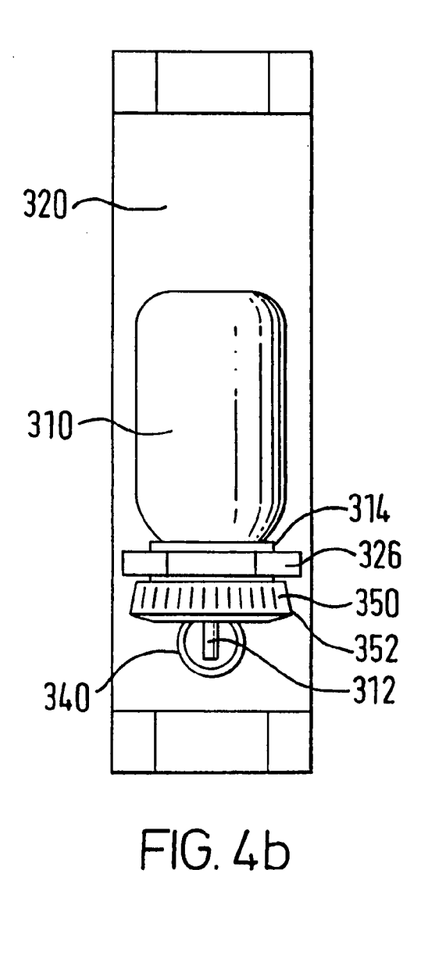

FIGS. 4*a* and 4*b* show a medicament dispenser herein mounted within an actuator housing 320. The actuator housing 320 is shown in the form of a laboratory test rig. It will be appreciated that the test rig can be adapted by way of workshop modifications to form a more recognizable product housing incorporating the same functional elements. FIG. 4*b* shows a sectional view of the dispenser and housing 320 taken along section B—B of FIG. 4*a*.

The medicament dispenser is suitable for use in a metered dose inhaler (MDI) for delivery of inhalable medicament. The dispenser comprises an aerosol can 310 having a dispenser outlet in the form of a metering valve 312. The valve gasket 314 is fixedly attached (typically by crimping) to the aerosol can body 310. The can suitably comprises a suspension of medicament in a propellant.

Figure 4C:
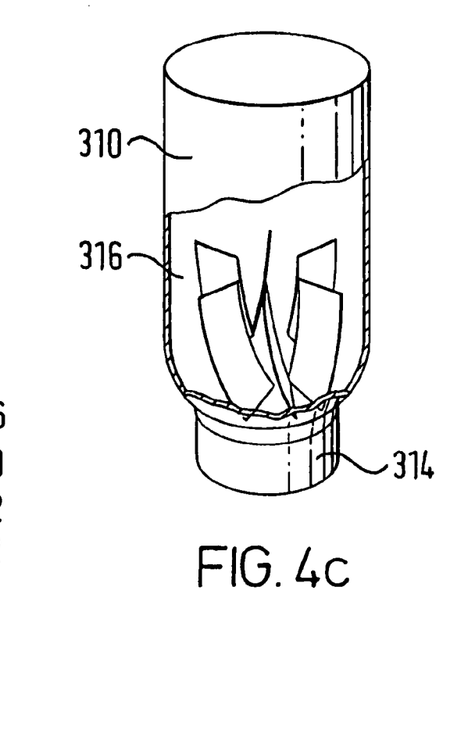
FIG. 4c shows a perspective cutaway view of a detail of the medicament dispenser of FIGS. 4a and 4b.

FIG. 4*c* shows a perspective cutaway view of a detail of the aerosol can of FIGS. 4*a* and 4*b*. The interior of the can may be seen to be provided with plural vanes forming a vane arrangement 316. The vane arrangement 316 acts such as to guide the flow of the fluid contents of the aerosol can 310.

The can 310 is mounted within horizontal support 326 which has a central aperture for receipt of the neck of the can such that the can 310 sits freely therein. The horizontal support 326 is fixed to the housing 320. Sleeve 350 is fixed to the exterior of the valve gasket 314 of can 310. The sleeve 350 is provided with bevelled lip 352 which connects with gear drive wheel 340 which is axially mounted to the housing 320. The gear drive wheel 340 is itself rotationally drivable by torsion spring drive 342. In other embodiments the torsion spring drive 342 may be replaced by any suitable drive motor.

Agitation of the aerosol can 310 is achievable by the following steps. The torsion spring drive 342 is actuated to drive the gear drive wheel 340. The gear drive wheel 340 drives rotation of the sleeve 350 and hence of the aerosol can 310. The rotation of the can 310 agitates the contents thereof assisted by the presence of the vane arrangement 316 within the can 310.

It may be appreciated that the torsion spring drive arrangement shown in the preceding figures may be implemented in an inhaler device such that torsion energy is provided thereto by a defined user movement. The movement could for example, be provided by a push button action. In an alternative, the device may be provided with a pivoted cover for a mouthpiece wherein the opening of the cover results in torsion energy being provided to the spring.

It may be appreciated that any of the parts of the dispenser which contact the medicament suspension may be coated with materials such as fluoropolymer materials which reduce the tendency of medicament to adhere thereto. Any movable parts may also have coatings applied thereto which enhance their desired movement characteristics. Frictional coatings may therefore be applied to enhance frictional contact and lubricants used to reduce frictional contact as necessary.

The medicament dispenser of the invention is suitable for dispensing medicament, particularly for the treatment of respiratory disorders such as asthma and chronic obstructive pulmonary disease. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g. s the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxotetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3, 4-diol (e.g. as maleate); α4 integrin inhibitors e.g. (2S)-3-[4-({[4-(aminocarbonyl)-1-piperidinyl]carbonyl}oxy)phenyl]-2-[((2S)-4-methyl-2{[2-(2-methylphenoxy)acetyl]amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament and/or to minimise the solubility of the medicament in the propellant. Preferred medicaments are selected from albuterol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) or formoterol (e.g. as the fumarate salt) in combination with an antiinflammatory steroid such as a beclomethasone ester (e.g., the dipropionate) or a fluticasone ester (e.g., the propionate) or budesonide. A particularly preferred combination is a combination of fluticasone propionate and salmeterol, or a salt thereof (particularly the xinafoate salt). A further combination of particular interest is budesonide and formoterol (e.g. as the fumarate salt).

It will be understood that the present disclosure is for the purpose of illustration only and the invention extends to modifications, variations and improvements thereto.

The application of which this description and claims form part may be used as a basis for priority in respect of any subsequent application. The claims of such subsequent application may be directed to any feature or combination of features described therein. They may take the form of product, method or use claims and may include by way of example and without limitation, one or more of the following claims:

The invention claimed is:

1. A medicament dispenser comprising:
   a housing;
   an aerosol medicament container having a dispensing outlet that comprises a metering valve, wherein said aerosol container contains a suspension of a medicament in a propellant;
   an agitator for agitating said container, the agitator being disposed outside of the container; and
   a driver for driving said agitator, wherein said driver comprises an energy store for storing energy which energy is releasable to drive the agitator;
   wherein the agitator couples mechanically to the container and the agitator is selected from the group consisting of a cam arrangement, a con-rod and crank arrangement and a gear drive arrangement.

2. A medicament dispenser according to claim 1, wherein the container is mounted for movement within the housing.

3. A medicament dispenser according to claim 2, wherein the container is rotatable within the housing.

4. A medicament dispenser according to claim 2, wherein the container is movable in a reciprocating fashion within the housing.

5. A medicament dispenser according to claim 1, wherein the agitator comprises a stepped cam.

6. A medicament dispenser according to claim 1, wherein the agitator comprises a snail cam.

7. A medicament dispenser according to claim 1, wherein the container comprises a guide to guide fluid flow within the container.

8. A medicament dispenser according to claim 7, wherein the guide comprises a vane arrangement.

9. A medicament dispenser according to claim 7, wherein the guide comprises a movable impeller.

10. A medicament dispenser according to claim 1, wherein said energy store comprises a battery.

11. A medicament dispenser according to claim 1, wherein the driver is responsive to a patient-actuable trigger.

12. A medicament dispenser according to claim 11, wherein said trigger comprises a button, switch or lever arrangement.

13. A medicament dispenser according to claim 11, wherein the trigger comprises a sensor which is adapted to sense the breath of a patient.

14. A medicament dispenser according to claim 13, wherein said sensor comprises a breath-movable element which is movable in response to the breath of a patient.

15. A medicament dispenser according to claim 14, wherein said breath-movable element is selected from the group consisting of a vane, a sail, a piston and an impeller.

16. A medicament dispenser according to claim 13, wherein said sensor comprises a pressure sensor for sensing the pressure profile associated with the breath of a patient.

17. A medicament dispenser according to claim 13, wherein said sensor comprises an airflow sensor for sensing the airflow profile associated with the breath of a patient.

18. A medicament dispenser according to claim 13, wherein said sensor comprises a temperature sensor for sensing the temperature profile associated with the breath of a patient.

19. A medicament dispenser according to claim 13, wherein said sensor comprises a moisture sensor for sensing the moisture profile associated with the breath of a patient.

20. A medicament dispenser according to claim 13, wherein said sensor comprises a gas sensor for sensing the oxygen or carbon dioxide profile associated with the breath of a patient.

21. A medicament dispenser according to claim 11, wherein dispensing from the dispensing outlet is responsive to a second patient-actuable trigger.

22. A medicament dispenser according to claim 21, wherein the patient-actuable triggers are coupled such that agitation and dispensing occurs in a sequential fashion.

23. A medicament dispenser according to claim 1, wherein, said propellant comprises liquefied HFA134a, HFA-227 or carbon dioxide.

24. A medicament dispenser comprising:
   a housing;
   an aerosol medicament container having a dispensing outlet that comprises a metering valve, wherein said aerosol container contains a suspension of a medicament in a propellant;
   an agitator for agitating said container, the agitator being disposed outside of the container; and
   a driver for driving said agitator, wherein said driver comprises an energy store for storing energy which energy is releasable to drive the agitator, said energy store comprising a biasable resilient member;

wherein the agitator couples mechanically to the container and the agitator is selected from the group consisting of a cam arrangement, a con-rod and crank arrangement and a gear drive arrangement.

25. A medicament dispenser according to claim 24, wherein said biasable resilient member is a spring.

26. A medicament dispenser according to claim 24, wherein said energy store comprises a clockwork mechanism.

* * * * *